(12) United States Patent
Van Etten

(10) Patent No.: US 6,854,694 B1
(45) Date of Patent: Feb. 15, 2005

(54) TUBE RETAINER

(76) Inventor: Wayne Van Etten, 45 Birch St., Kingston, NY (US) 12401

( * ) Notice: Subject to any disclaimer, the term of this patent is extended or adjusted under 35 U.S.C. 154(b) by 0 days.

(21) Appl. No.: 10/700,139

(22) Filed: Nov. 3, 2003

(51) Int. Cl.$^7$ .................................................. F16L 3/12
(52) U.S. Cl. ........................ 248/75; 248/62; 248/74.1; 403/324
(58) Field of Search ........................... 248/73, 74.1, 75, 248/62, 228.6, 231.71; 24/16 R, 278, 19, 268; 411/493, 496, 497; 403/109.6, 324, 379.5

(56) References Cited

U.S. PATENT DOCUMENTS

| | | | |
|---|---|---|---|
| 1,599,278 A | * 9/1926 | Kass | 138/99 |
| 1,735,192 A | * 11/1929 | Williams et al. | 248/74.1 |
| 4,141,524 A | 2/1979 | Corvese, Jr. | |
| 4,449,527 A | 5/1984 | Hinton | |
| 4,460,140 A | * 7/1984 | Ramazzotti et al. | 248/75 |
| 4,707,906 A | 11/1987 | Posey | |
| 5,140,983 A | 8/1992 | Jinotti | |
| 5,364,281 A | * 11/1994 | Leto | 439/100 |
| 5,555,881 A | 9/1996 | Rogers et al. | |
| 5,803,079 A | 9/1998 | Rogers et al. | |
| 6,082,583 A | 7/2000 | Bussell et al. | |
| 6,378,522 B1 | 4/2002 | Pagan | |
| 6,398,445 B1 | * 6/2002 | Matali Badia | 403/109.6 |
| 6,575,656 B2 | * 6/2003 | Suh | 403/109.6 |
| 6,668,865 B2 | * 12/2003 | Miyamoto et al. | 138/108 |

FOREIGN PATENT DOCUMENTS

EP        EP-489625 A1 *  6/1992

* cited by examiner

*Primary Examiner*—Anita King
*Assistant Examiner*—Jon Szumny

(57) ABSTRACT

A tube retainer is provided for use with a corrugated tube to permit movement of the corrugated tube through the tube retainer in only one direction. The tube retainer includes a cylindrical housing with an outer surface and a concentric opening through it. A groove is circumferentially located about the cylindrical housing. An O-ring is located in the groove. Pins are located under the O-ring in the holes which extend from the groove into the opening. Each pin has a transitional end which extends into the opening and the transitional end rides up and down on the corrugations which permits movement of the corrugated tube in only one direction. The transitional end may be beveled or contoured or have other possible configurations.

19 Claims, 3 Drawing Sheets

TUBE RETAINER

BACKGROUND OF THE INVENTION

FIELD OF THE INVENTION

This invention relates to a device for retaining a tube and, more specifically, a device for retaining a corrugated tube so that the corrugated can only be pulled in only one direction.

PRIOR ART

Medical patients having certain conditions require that they be supplied with air or oxygen through a tube placed in the trachea. Such a device is at best uncomfortable but should the patient move, the tube can be pulled from the trachea. This creates a painful and dangerous situation. If a restricted amount of tubing is provided, the least movement by the patient will dislocate the tube. If extensive tubing is provided, the patient can become entangled in the tube which can readily result in the removal of the tube. It is also important that the tube, for whatever reason, not be pulled by some other event remote from the patient, such as the tube being inadvertently pulled by a third part such as a visitor or medical attendant. Frequently, the tube is placed in a U-shape below the patient to trap fluid. This trapped fluid weights heavily and pulls the tube from the patient.

Various patents have been issued concerning the use of a trachea tube but not specifically directed to a one-way release of a tube for trachea feeding. Such patents have not been directed to a device for preventing movement of such a tube away from the patient.

The objects of this invention are as follows:

To provide a device for permitting a tube to be pulled in only one direction.

To provide a device for controlling the movement of a tube which can be readily mounted in a convenient location.

To provide a device for controlling the movement of a tube which is simple in construction, economical and dependable.

These and other objects will be apparent to those skilled in the art based upon the description of the preferred embodiment.

SUMMARY OF THE INVENTION

A tube retainer is described for use with a corrugated tube to permit movement of the corrugated tube through the tube retainer in only one direction. The tube retainer includes a cylindrical housing with an outer surface and an opening through it that is concentrically located in the cylindrical housing, the opening having an inner surface. There is at least one hole extending radially from the inner surface to the outer surface. A pin which has a top surface and beveled end is mounted to slide in the hole. The pin has a transitional end which extends beyond the inner surface into the opening. A means is also provided for forcing the pin toward the opening.

DESCRIPTION OF THE NUMERALS

| NUMERAL | DESCRIPTION |
| --- | --- |
| 11 | Tube |
| 13 | Cylindrical Housing |
| 15 | Opening |
| 17 | Inner Surface |
| 19 | Outer Surface |
| 21 | Front Surface |
| 23 | Rear Surface |
| 25 | Groove |
| 26 | Wall |
| 27 | Hole |
| 29 | Upper Section |
| 31 | Lower Section |
| 33 | Pin |
| 35 | Junction |
| 37 | Upper Portion |
| 39 | Lower Portion |
| 41 | Outside Surface |
| 43 | Inside Surface |
| 45 | Top Surface |
| 47 | Channel |
| 49 | Rounded Base |
| 51 | Beveled End |
| 53 | Short Side |
| 55 | Long Side |
| 56 | Contoured End |
| 57 | O-Ring |
| 61 | External Surface |
| 63 | Peaks |
| 65 | Valleys |
| 67 | Bracket |
| 69 | Ring |
| 71 | Arm |
| 73 | First Leg |
| 75 | Second Leg |
| 77 | Third Leg |
| 79 | Threaded Opening |
| 81 | Bolt |
| 83 | Stud Bolts |
| 85 | Bolt Holes |
| 87 | Threaded Holes |

DETAILED DESCRIPTION OF THE PREFERRED EMBODIMENT

Figure 1:
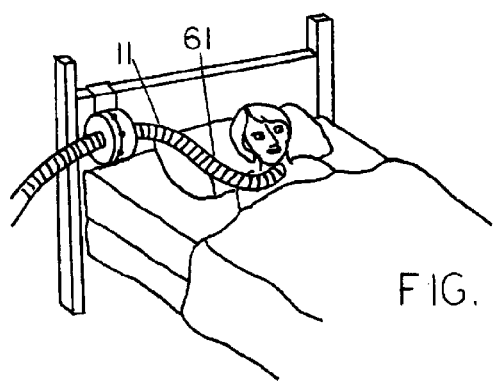
FIG. 1 is a pictorial view of the Tube Retainer mounted on a bed showing a tube inverted in the trachea of a patient, the tube being retained by the Tube Retainer.

Referring now to FIG. 1, a patient is portrayed in a bed with a tube 11, shown more specifically as a trachea tube, inserted the trachea of the patient. The Tube Retainer, however, may be used for a variety of purposes where a tube is to be restricted as to movement in one direction. The Tube Retainer, as shown in FIG. 1, is mounted on a bed and the tube 11 is shown mounted in the Tube Retainer. The purpose of the Tube Retainer is to permit the tube 11 to be fed from the Tube Retainer to the patient should the patient move in the bed in such a manner as to require an additional portion of the tube 11. By the Tube Retainer permitting such an additional amount of the tube 11 to be fed toward the patient, pulling the tube 11 from the trachea of the patient is avoided.

Figure 2:
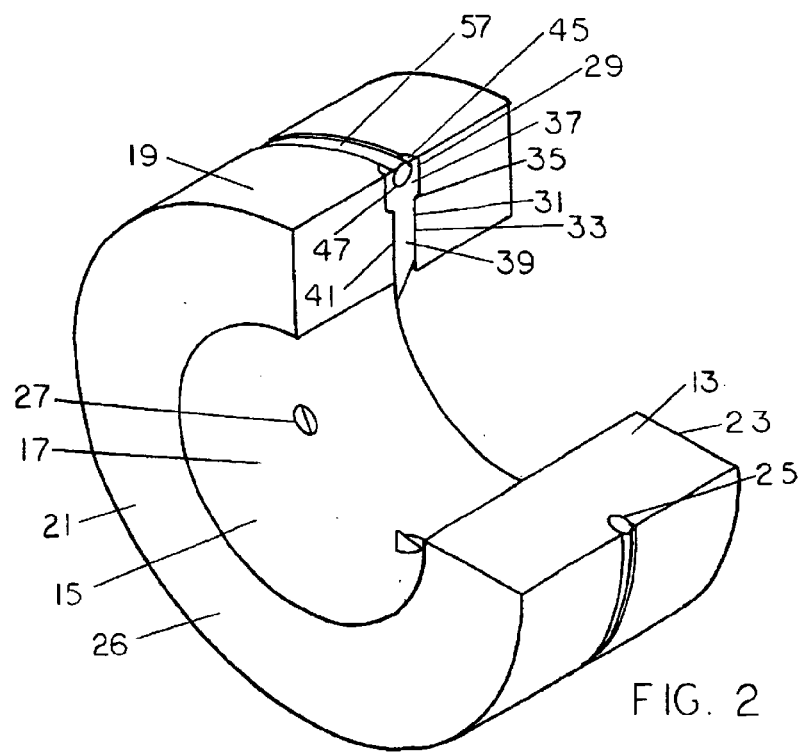
FIG. 2 is a pictorial view of the Tube Retainer with a portion cut away to show the inside of the Tube Retainer.
Figure 2A:
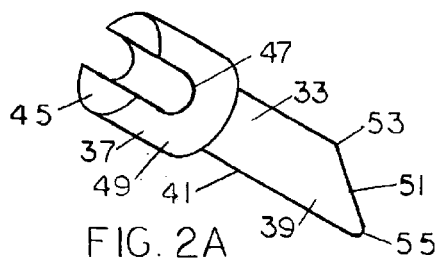
FIG. 2A is a perspective of the pin with a beveled end.

Now referring to FIG. 2, the Tube Retainer is shown in pictorial form with a quarter of the Tube Retainer cutaway. The Retaining Device includes a cylindrical housing 13 with an opening 15 through the cylindrical housing 13 which is generally concentric. The opening 15 has an inner surface 17 which is also cylindrical. The cylindrical housing 13 requires only limited length with an outer surface 19 which has a circumference which is cylindrical and, as stated, has an opening 15 through it which is generally concentric with the outer surface 19. The Tube Retainer has front surface 21 and a rear surface 23 and the opening 15 extends between the front surface 21 and the rear surface 23. A groove 25 is located about the circumference of the outer surface 19 and the groove 25 is preferably located midway between the front surface 21 and the rear surface 23 of the cylindrical housing 13. The wall 26 between the inner surface 17 and the outer surface 19 of the cylinder is comparatively thick.

A series of holes 27 which extend radically from the the inner surface 17 to the outer surface 19 are located in the groove 25. The holes 27 preferable have a circular cross section. At the outer surface 19, the holes 27 have an upper section 29 with a comparatively larger diameter than the lower section 31 of the holes 27 which is the remaining length of each hole 27 from the upper section 29 through the inner surface 17. The comparatively larger diameter of the upper section 29 provides space to countersink a pin 23 to be subsequently described. The upper section 29 which can also be described as the countersunk section, is a minor part of the length of each hole 27 and the lower section 31 is substantially longer but smaller in cross section area than the upper section 29. At the junction 35 of the upper section 29 and the lower section 31, the upper section 29 tapers sharply toward the lower section 31.

Figure 2C:
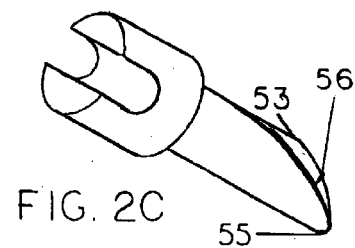
FIG. 2C is a perspective view of the pin with a contoured end.
Figure 2B:
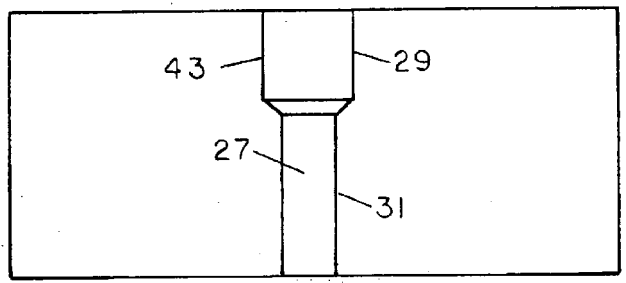
FIG. 2B is a cross-sectional view of one hole through the wall.
Figure 3A:
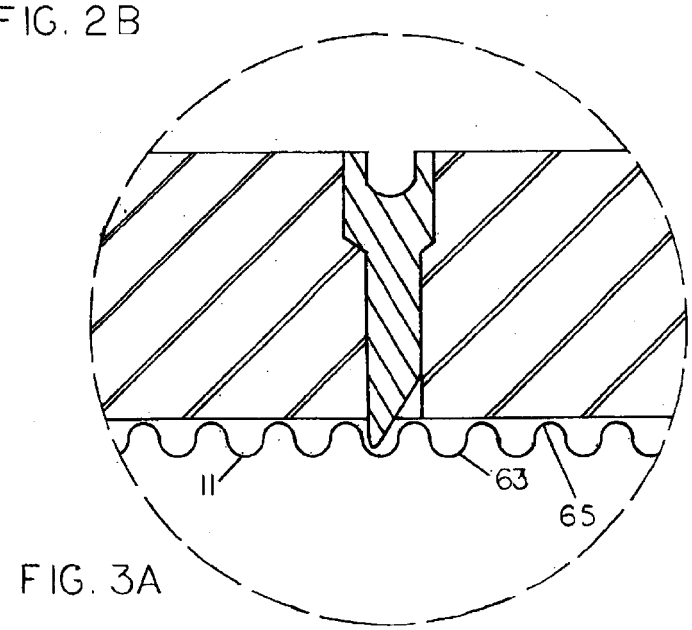
FIG. 3A is a an enlarged cross-sectional view of the tube showing the peaks and valleys of the corrugation and the beveled end of the pin in the valleys.
Figure 3:
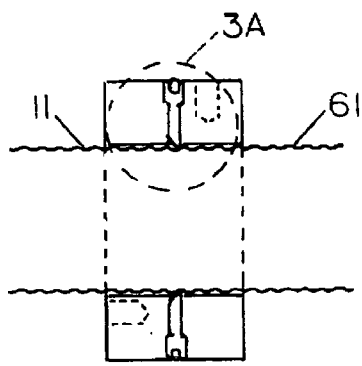
FIG. 3 is a cross sectional view of the Tube Retainer with a tube which is corrugated in it.
Figure 4:
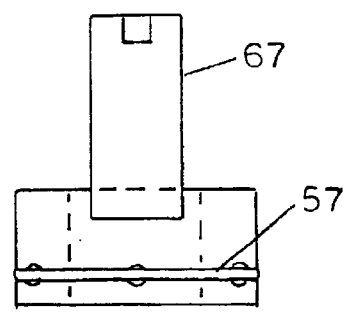
FIG. 4 is a top view of the Tube Retainer with a mounting bracket affixed to it.
Figure 5:
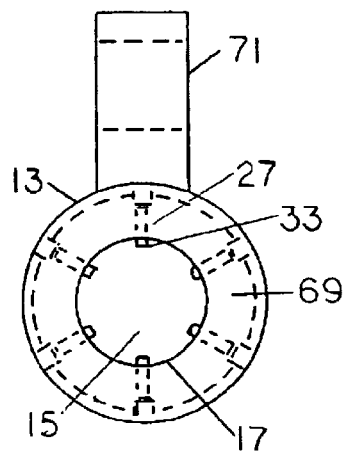
FIG. 5 is a front elevation of the Tube Retainer with a mounting bracket attached to it.
Figure 6:
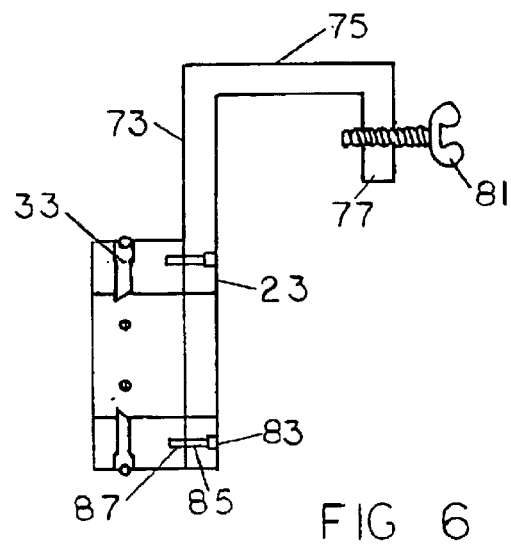
FIG. 6 is a cross-sectional view of the Tube Retainer with a mounting bracket attached to it.

Fitted to slide in each of the holes 27 is the pin 33 previously discussed. Each pin 33 has a upper portion 37 and a lower portion 39 and has an external configuration to fit within and slidably conform to the hole 37. The outside surface 41 of each pin 33 is essentially the same as the inside surface 43 of each hole 27. The upper portion 37 of each pin 33 has a top surface 45 which has a channel 47 in it with a rounded base 49 and which aligns with the outer surface 19. The channel 47 has the same size and configuration as the groove 25. The lower portion 39 of each pin 33 is cut off at an acute angle of approximately sixty degrees to the length of each pin to form a beveled end 51. The beveled end 51 of the pin 33 extends into the opening 15. Preferable approximately a half of the beveled end 51 protrudes into the opening 15 when the upper portion 37 of each pin 13 is fully set in the upper section 29 of each hole 27. The beveled end 51 has a short side 53 and a long side 55. The long side 55 is located toward the front surface 21 of the Tube Retainer while the short side 53 is located toward the rear surface 33 of the cylindrical housing 13. The beveled end 51 may be, as shown in FIG. 2C be replaced with a contoured end 56. The short side 53 and the long side 55 may have various transitional ends of which the beveled end 51 and the contoured end 56 are but two examples. The groove 25 in the top surface 45 of the pin 33 is substantially at right angles to the beveled end 51 or contoured end or other transitional end.

The number of pins 33 may vary but the pins 33 are preferably located generally equidistant from one another about the outer surface 19 of the cylindrical housing 13 and less pins 33 can be used in some circumstances and even just one pin 33 could suffice, particularly where only limited retention is desired.

An O-ring 57 is placed in the groove 25 about the outer surface 19 and in the channels 47 in the top surface 45 of each of the pins 33. The O-ring 57 forces each pin 33 down into its respective hole 27 toward the opening 15 and provides resistance to each pin 33 to prevent each pin 33 from moving upwardly away from the opening 15 and out of and beyond the outer surface 19.

The tube 11, most likely to be used as a trachea tube, is corrugated to provide flexibility. The tube 11, which has an external surface 61, has peaks 63 and valleys 65 consistent with the corrugation. The tube 11 is fed into the opening 15 at the rear surface 23 of the cylindrical housing 13. The tube 59 leaves the cylindrical housing 13, on the front surface 21 which is closest to the place where the end of the tube 59 is to be inserted. In FIG. 1 this place is shown as the trachea of a patient in bed. As the tube 11 progresses from the rear surface 23 toward the front surface 21, the pin 33 is forced down into the valley 65 and then the short side 53 of the beveled end 51 or other transitional end of the pin 33 rides up to the peak 63 of the corrugation of the tube 11 against the force of the O-ring 57. However, if the tube 59 is pulled in the opposite direction, namely from the front surface 21 to the rear surface 23 the long side 55 of the pin 33 will not ride up over the peaks 63 of the tube 11 thereby prohibiting movement of the tube 11 in that direction.

By placing the inner surface 17 toward a patient, the tube 11 can be fed toward the patient, as the need may arise such as from the movement of the body of the patient but the tube 59 cannot be accidentally pulled through the Tube Retainer from the patient.

As best seen in FIG. 3 through FIG. 6, a bracket 67 for mounting the Tube Retainer may be included as part of the Tube Retainer. The bracket 67 includes a ring 69 that has the size and configuration of the cylindrical housing 13. An arm 71 has a first leg 73 which extends from the ring 69 for a short distance in the same plane as the ring 69 is located. The arm 71 further has a second leg 75 which substantially extends at right angles from the first leg 73 away from the ring 69 and then has a third leg 77 which turns back at a right angle to the second leg 71 and generally parallel to the first leg 73 for a short distance. As a result, the bracket 67 has an inverted U-shape. A threaded opening 79 in the third leg 77 permits use of a bolt 81 such as a wing bolt or clamping the bracket 69 to a part of a bed or other fixed object.

The bracket 67 is affixed to the cylindrical housing 13 by a plurality of bolts 83 which are placed in bolt holes 85 through the ring 69 and are threaded into threaded openings 87 in the front surface 21 of the cylindrical housing 13.

It is to be understood that the drawings and description matter are in all cases to be interpreted as merely illustrative of the principles of the invention, rather than as limiting the same in any way, since it is contemplated that various changes may be made in various elements to achieve like results without departing from the spirit of the invention or the scope of the appended claims.

What is claimed is:

1. A tube retainer for use with a corrugated tube to permit movement of the corrugated tube through the tube retainer in only one direction, said tube retainer comprising:

a cylindrical housing with an outer surface and an opening through it that is concentrically located in the cylindrical housing, the opening having an inner surface, the cylindrical housing having a groove located about the outer surface and further having at least one hole extending radially from the inner surface to the groove;

a pin having a top surface and a short side and a long side, the pin being mounted to slide in the hole, the pin further having a transitional end between the long side and the short side, the transitional end extending beyond the inner surface into the opening; and means for forcing the pin toward the opening.

2. The tube retainer according to claim 1 wherein the hole has an upper section with a cross-sectional area and a lower section with a cross-sectional area smaller than the cross-sectional area of the upper section.

3. The tube retainer according to claim 1 wherein the hole has an upper section with a cross-sectional area and a lower section with a cross-sectional area smaller than the cross-sectional area of the upper section and the lower section is longer than the upper section.

4. The tube retainer according to claim 1 wherein there is a channel in the top surface of the pin, the channel having substantially the same size and configuration as the channel groove.

5. The tube retainer according to claim 1 wherein there is a channel in the top surface of the pin, the channel having substantially the same size and configuration as the groove and wherein the means for forcing the pin toward the opening is an O-ring located in the groove and the channel.

6. The tube retainer according to claim 1 wherein the transitional end is a beveled end.

7. The tube retainer according to claim 1 wherein the transitional end is a contoured end.

8. A tube retainer for use with a corrugated tube to permit movement of the corrugated tube through the tube retainer in only one direction, said tube retainer comprising:

a cylindrical housing with an outer surface and having a front surface and a rear surface and an opening through it that is concentrically located in the cylindrical housing extending between the front surface and the rear surface, the opening having an inner surface and a groove that is rounded is located on the outer surface about the cylindrical housing and further having a plurality of holes extending radially about the inner surface to the groove in the outer surface, each hole having and upper section adjacent the outer surface and a lower section adjacent the inside surface, the lower section having a smaller cross-sectional area than that of the upper section, the lower section being longer than the upper section;

pins each having a top surface and a short side and a long side, the each pin being mounted to slide in one of the holes, each pin having a channel across its top surface and having a transitional end between the long side and the short side, the channel having substantially the same size and shape as the groove, the transitional end extending beyond the inner surface into the opening, the long side being closer to the front surface than the short side; and an O-ring located in the groove and the channel of the pin, the channels being located generally at a right angel to the transmittal end.

9. A tube retainer according to claim 8 wherein the transitional end is a beveled end.

10. A tube retainer according to claim 8 wherein the transitional end is a contoured end.

11. The tube retainer for use with a corrugated tube to permit movement of the corrugated tube through the tube retainer in only one direction, said tube retainer comprising:

a cylindrical housing with an outer surface and an opening through it that is concentrically located in the cylindrical housing, the opening having an inner surface and a groove is located about the cylindrical housing and further having at least one hole extending radially from the inner surface to the outer surface, the hole being larger adjacent the outer surface;

a pin having a top surface and a short side and a long side, the pin being mounted to slide in the hole, the pin further having a channel across its top surface and having a transitional end between the long side and the short side, the transitional end extending beyond the inner surface into the opening; and an O-ring located in the groove and the channel of the pin, the channel being located generally at a right angles to the Transitional end.

12. The tube retainer according to claim 11 wherein the hole extends from the groove on the outer surface.

13. The tube retainer according to claim 11 wherein the hole has an upper section with a cross-sectional area and a lower section with a cross-sectional area smaller than the cross-sectional area of the upper section and the lower section is longer than the upper section.

14. The tube retainer according to claim 11 wherein the hole and the pin have a circular cross section.

15. The tube retainer according to claim 11 wherein the transitional end is a beveled end.

16. The tube retainer according to claim 11 wherein the transitional end is contoured end.

17. The tube retainer according to claim 11 wherein the transitional end is a beveled end which has an acute angle of approximately sixty degrees.

18. The tube retainer according to claim 11 wherein, the channel has substantially the same size and configuration as the groove.

19. The tube retainer for use with a corrugated tube to permit movement of the corrugated tube through the tube retainer in only one direction, said tube retainer comprising:

a cylindrical housing with an outer surface and an opening through it that is concentrically located in the cylindrical housing, the opening having an inner surface and further having at least one hole extending radically from the inner surface to the outer surface the hole having an upper section with a cross-sectional area and a lower section with a cross-sectional area smaller than the cross-sectional area of the upper section and the lower section being longer than the upper section;

a pin having a top surface and a short side and a long side, the pin being mounted to slide in the hole, the pin further having a transitional end between the long side and the short side, the transitional end extending beyond the inner surface into the opening; and means for forcing the pin toward the opening.

* * * * *